(12) United States Patent
Dalmases Barjoan et al.

(10) Patent No.: US 8,129,522 B2
(45) Date of Patent: Mar. 6, 2012

(54) METHOD FOR PREPARING A MIXED SOLVATE OF OLANZAPINE

(75) Inventors: Pere Dalmases Barjoan, Sant Feliu de Llobregat (ES); Reyes Herbera Espinal, Agramunt (ES)

(73) Assignee: Inke, S.A., Castellbisbal (ES)

( * ) Notice: Subject to any disclaimer, the term of this patent is extended or adjusted under 35 U.S.C. 154(b) by 639 days.

(21) Appl. No.: 12/160,004

(22) PCT Filed: Dec. 20, 2006

(86) PCT No.: PCT/EP2006/070028
§ 371 (c)(1),
(2), (4) Date: Apr. 6, 2009

(87) PCT Pub. No.: WO2007/077134
PCT Pub. Date: Jul. 12, 2007

(65) Prior Publication Data
US 2009/0318683 A1    Dec. 24, 2009

(30) Foreign Application Priority Data
Jan. 5, 2006    (ES) .................. 200600059

(51) Int. Cl.
*C07D 495/04*    (2006.01)
(52) U.S. Cl. ...................................... 540/557
(58) Field of Classification Search ............ 540/557
See application file for complete search history.

(56) References Cited
FOREIGN PATENT DOCUMENTS
WO    03/097650    11/2003
WO    2006/013435    2/2006

OTHER PUBLICATIONS

Calligaro et al., "The Synthesis and Biological Activity of Some Known and Putative Metabolites of the Atypical Antipsychotic Agent Olanzapine (LY150053)" Bioorganic & Medicinal Chemistry Letters, vol. 7, No. 1, pp. 25030, 1977.

*Primary Examiner* — Brenda Coleman
(74) *Attorney, Agent, or Firm* — Cozen O'Connor

(57) ABSTRACT

An improved method is provided for preparing a mixed solvate of olanzapine/water/tetrahydrofuran in a proportion of 1:1:1/2. Said improvement is characterised in that said mixed solvate is basically prepared by means of methylation of the N-desmethylolanzapine with dimethyl sulphate, using tetrahydrofuran and water as solvents.

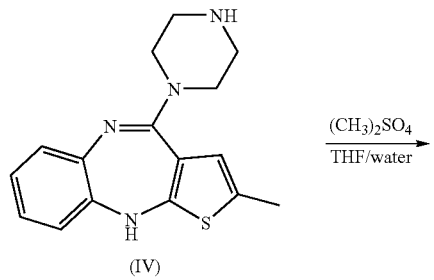

(IV)

$(CH_3)_2SO_4$ / THF/water

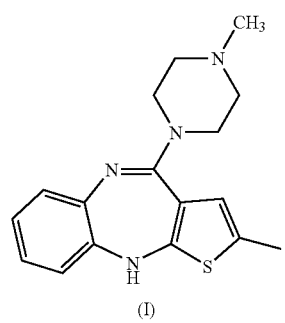
(I)

7 Claims, No Drawings

METHOD FOR PREPARING A MIXED SOLVATE OF OLANZAPINE

This application is the U.S. national stage of PCT Application No. PCT/EP2006/070028, filed Dec. 20, 2006, which claims priority of Spanish Application No. P200600059, filed Jan. 5, 2006, the contents of which are incorporated herein in their entirety.

FIELD OF THE INVENTION

The present invention relates to an improved method for preparing a mixed solvate of olanzapine.

In particular, the present invention relates to an improved method for preparing said mixed solvate of olanzapine/water/tetrahydrofuran in a proportion of 1:1:1/2.

BACKGROUND OF THE INVENTION

Olanzapine is a thienobenzodiazepine of formula (I):

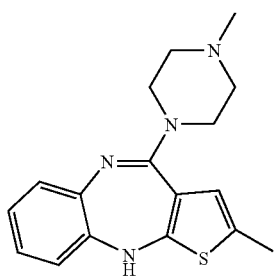

that acts as an antagonist on receptors of dopamine D1, D2, D3, D4 and D5; of serotonine 5-HT2 and 5HT3; alpha-1-adrenergics, cholinergics and H1 histaminergics.

Olanzapine was disclosed for the first time in patent EP0454436B1, in which said thienobenzodiazepine was prepared from 4-amino-2-methyl-10H-thieno[2,3-b][1,5]benzodiazepine and N-methylpiperazine in DMSO/toluene, followed by isolation of the olanzapine by addition of water and crystallisation with acetonitrile.

Patent EP0733635A1 discloses two polymorphic forms of olanzapine: Form I (metastable) and Form II (stable), Form I being that obtained in the first patent EP0454436B1.

The metastable character of Form I relates to a change of colour under ambient storage conditions.

Patents EP0733634A1, U.S. Pat. No. 5,703,232 and EP0831098A2 claim the preparation of hydrated species and of solvates from olanzapine alcohols and the use thereof for preparing Form II (stable) of olanzapine, although in U.S. Pat. No. 5,703,232 the stable form is called Form I (while in the other documents the stable form is referred to as Form II).

U.S. Pat. No. 5,637,584 claims the solvate of dichloromethane of olanzapine and a method for preparing it.

Finally, patents WO0218390A1, WO03097650A1, WO03055438A2, WO03101997 and WO2004006933A2 claim the preparation of Form I olanzapine. In patent WO0218390A1 Form I of olanzapine is prepared from the dihydrate I, from the monohydrate I or from Form II, by crystallisation in dichloromethane. In patent WO03097650A1, Form I is prepared by extraction and subsequent purification with dichloromethane of olanzapine prepared by condensation of 4-amino-2-methyl-10H-thieno[2,3-b][1,5]benzodiazepine and N-methylpiperazine. Said patent claims a mixed solvate of dichloromethane/water and a mixed solvate of DMSO/water. In patent WO03055438A2, Form I is prepared by successive crystallisations and decolouration in C1-C4 alcohols. In patent WO03101997, Form I is prepared by precipitation from a mixture of an organic solvent in a basic medium such as toluene and methanolic soda, seeding with Form I itself. In WO2004006933A2, Form I is prepared by crystallisation of a mixture of solvents that contain IPA. In some of the preceding patents, the Form I obtained is described as stable to colour changes.

DESCRIPTION OF THE INVENTION

The object of the present invention is to provide an alternative and improved method for preparing the mixed solvate of olanzapine/water/tetrahydrofuran in a proportion of 1:1:1/2 (I):

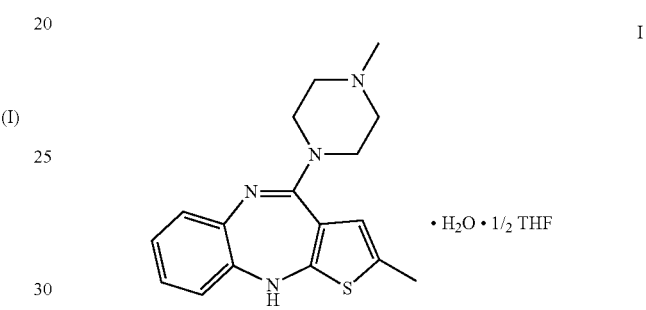

In consequence, a first aspect of the present invention relates to improvements in the object of the patent no. 200401850 (WO2006013435), for "Mixed solvate of olanzapine, method for preparing it and method for preparing Form I of olanzapine therefrom", characterised in that a new method is provided for preparing said mixed solvate that essentially consists in methylation of the N-desmethylolanzapine with dimethyl sulphate, using tetrahydrofuran and water as solvents.

DETAILED DESCRIPTION OF THE INVENTION

For a better understanding of the improvements in the object of the present invention, there follows a brief summary of the object of the patent no. 200401850.

The object of the patent is to provide a mixed solvate of olanzapine/water/tetrahydrofuran in a proportion of 1:1:1/2 of formula (I):

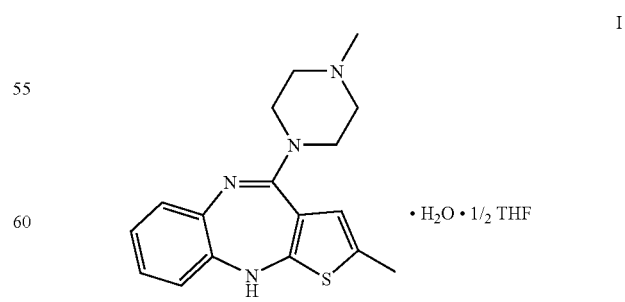

which is identified by its powder X-ray diffractogram. Table 1 below shows the peaks observed in an X-ray diffractogram using a PHILIPS X'Pert automatic diffractometer for crystalline powder provided with a Cu tube and a secondary graphite monochromator (wavelength KαCu, 1,5419 Å).

The X-ray diffractogram of the solvate is characterised by the position (°2θ), the interplanar spacing d and the relative intensities $I/I_0$. Said diffraction pattern reveals the following characteristic peaks of said mixed solvate.

TABLE 1

| Position (°2θ) | d (m$^{-10}$) | $I/I_0$ |
|---|---|---|
| 8.83 | 10.010 | 100 |
| 9.05 | 9.777 | 5 |
| 12.87 | 6.879 | 7 |
| 13.87 | 6.383 | 16 |
| 14.19 | 6.243 | 7 |
| 14.43 | 6.140 | 7 |
| 14.97 | 5.920 | 4 |
| 18.12 | 4.896 | 61 |
| 18.50 | 4.795 | 18 |
| 18.77 | 4.727 | 21 |
| 19.43 | 4.570 | 53 |
| 19.62 | 4.525 | 14 |
| 19.88 | 4.467 | 20 |
| 20.20 | 4.396 | 13 |
| 20.46 | 4.341 | 13 |
| 21.33 | 4.166 | 9 |
| 22.58 | 3.938 | 12 |
| 22.98 | 3.870 | 35 |
| 23.31 | 3.817 | 48 |
| 24.23 | 3.674 | 19 |
| 24.79 | 3.592 | 35 |
| 25.89 | 3.441 | 7 |
| 26.61 | 3.350 | 5 |
| 27.17 | 3.282 | 4 |
| 27.29 | 3.268 | 4 |
| 27.79 | 3.211 | 10 |
| 27.94 | 3.194 | 7 |
| 28.46 | 3.136 | 4 |
| 30.11 | 2.968 | 9 |
| 30.95 | 2.890 | 8 |
| 32.38 | 2.765 | 4 |
| 33.31 | 2.689 | 7 |
| 33.59 | 2.668 | 5 |
| 37.75 | 2.383 | 4 |
| 39.35 | 2.290 | 5 |

The ES200401850 patent also relates to a method for preparing said mixed solvate of olanzapine/water/tetrahydrofuran in the proportion 1:1:1/2, which includes solvating a crude anhydrous olanzapine with a mixture of tetrahydrofuran/water in a proportion of between 1:10 and 10:1 v/v, at a temperature between 20 and 80° C.

Another alternative method that is described in the ES200401850 patent for preparing said mixed solvate is by starting from condensation of the 4-amino-2-methyl-10H-thieno[2,3-b][1,5]benzodiazepine hydrochloride (II) with N-methylpiperazine (III):

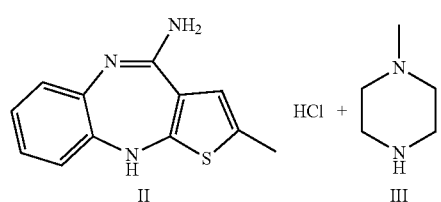

followed by distillation of the remaining N-methylpiperazine and, finally, treating the resulting crude product with a mixture of tetrahydrofuran/water in a proportion of between 1:10 and 10:1 v/v, precipitating the mixed solvate of olanzapine/water/tetrahydrofuran in the proportion 1:1:1/2.

The ES200401850 patent also relates to the preparation of Form I olanzapine from the mixed solvate of olanzapine/water/tetrahydrofuran in the proportion 1:1:1/2. Said method comprises drying the solvate in vacuo at a pressure that ranges between 1 and 40 mmHg at a temperature controlled between 10 and 50° C.

The present invention refers to an alternative method for preparing the mixed solvate of olanzapine/water/tetrahydrofuran in the proportion 1:1:1/2, in which said improvements are characterised in that the following stages are carried out:

a) Condensation of the compound of formula (IIa) with piperazine of formula (IIIa) in the presence of at least one aprotic solvent, followed by purification by crystallisation in anhydrous toluene:

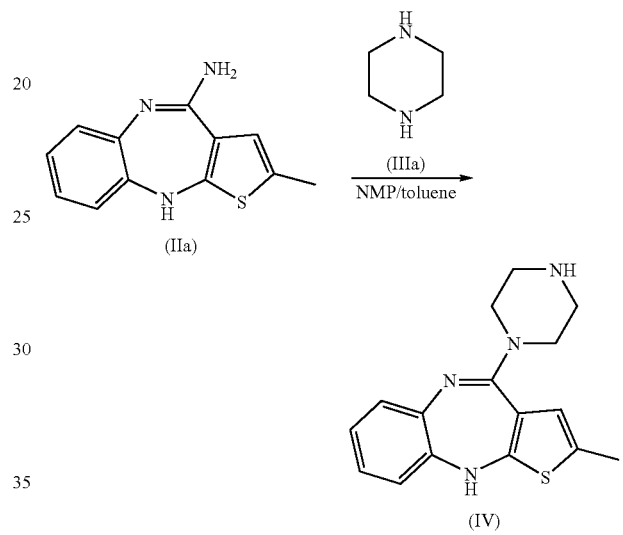

b) Methylation of the N-desmethylolanzapine of formula (IV) with dimethyl sulphate in the presence of tetrahydrofuran and water as solvents:

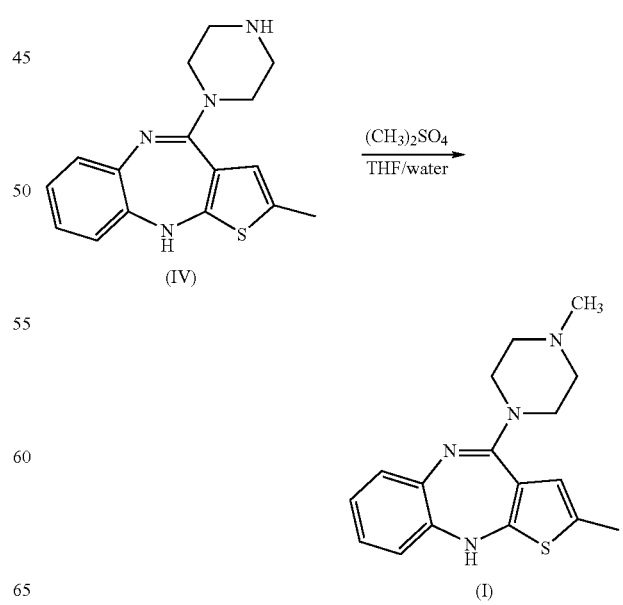

b) Direct obtaining of the mixed solvate of olanzapine/water/THF c) Drying and obtaining of Form I of Olanzapine.

The product (IV), N-desmethylolanzapine, is known and, therefore, its preparation lies within the scope of a person skilled in the subject.

In the present invention the N-desmethylolanzapine is purified by crystallisation and then in a second stage submitted to a methylation reaction with dimethyl sulphate and then olanzapine in THF solution is obtained. By means of addition of water the mixed solvate of olanzapine/water/THF is formed, and later isolated.

The improvements in this method are based on the fact that the utilisation of N-desmethylolanzapine as intermediate product allows this compound to be purified by crystallisation in anhydrous toluene so as to improve the profile of impurities present in the mixed solvate of olanzapine/water/THF, which in turn allows a high-purity Form I of olanzapine to be obtained.

Advantageously, the reaction of stage a) is carried out with piperazine in the presence of aprotic solvents such as N-methylpyrrolidone (NMP) and/or toluene or mixtures thereof, at a temperature between 50° C. and 150° C., preferably between 120 and 135° C. The product obtained is purified by crystallisation in anhydrous toluene. In stage b) the reaction is carried out in the presence of one or more inorganic bases as hydroxides and carbonates of alkaline metals, using as solvent a mixture of THF and water. The reaction takes place by addition of a methylating agent, preferably methyl sulphate, at a temperature between 0° C. and 30° C., preferably between 5° C. and 15° C., under inert atmosphere. Once completed, the reaction is carried out a work-up with water and dilute hydrochloric acid, achieving a solution of olanzapine in tetrahydrofuran.

The mixed solvate of olanzapine/water/THF is prepared by adding water to said solution.

The stages of conversion of the mixed solvate into Form I of olanzapine by drying already forms part of the content of the patent no. 200401850.

There follows below an embodiment of the present invention that, by way of non-restrictive example, describes the preparation of the mixed solvate of olanzapine/THF/water.

EXAMPLE

Example 1

To a solution precooled to 10° C. of 0.125 kg (3.125 moles) of sodium hydroxide and 0.261 kg (1.891 moles) of potassium carbonate in 1.66 L of water are added 8 L of tetrahydrofuran and 1.0 kg (3.160 moles) of 2-methyl-4-(1-piperazinil)-10H-thieno[2,3-b][1,5]benzodiazepine (N-desmethylolanzapine purified by crystallisation in anhydrous toluene). To the resulting suspension 0.484 kg of dimethyl sulphate dissolved in 0.83 L of tetrahydrofuran are added at 10° C. and under nitrogen atmosphere over the course of 2-3 hours. Once the addition has finished, the stirring is maintained at 10° C. for 5 hours and the solution then heated to 30° C. with stirring continued for 30 min. Then, 0.666 L of water and 0.075 L of aqueous hydrochloric acid at 35% are added and the suspension is heated at 50° C. through to total dissolution, providing a two-phase mixture. The lower aqueous phase is decanted and the upper organic phase is filtered at 45-50° C. 4.6 L of tetrahydrofuran are distilled in vacuo, and 4.3 L of water are added and distillation of the tetrahydrofuran is completed. 1.85 L of tetrahydrofuran is added and heated at reflux. It is cooled to 5° C. and the resulting solid is filtered and washed twice with 1 L of water. The solid obtained is dried in an air oven at 40° C. to constant weight, providing 0.85 kg (73%) of the mixed solvate of olanzapine/water/tetrahydrofuran in the proportion 1:1:1/2.

If wished, the solvate obtained is purified by dissolution at reflux in 3.4 L of THF followed by addition of 0.85 L of water. After cooling at 20-25° C. for one hour and, afterwards, at 0° C. for a further hour, the solid is filtered and dried in an air oven at 42° C. to constant weight to provide 750 g of mixed solvate of olanzapine/water/tetrahydrofuran in the proportion 1:1:1/2 with less than 0.2% of total impurities by HPLC.

The invention claimed is:

1. A method for preparing a mixed solvate of olanzapine/water/tetrahydrofuran in a proportion of 1:1:1/2 of formula (I):

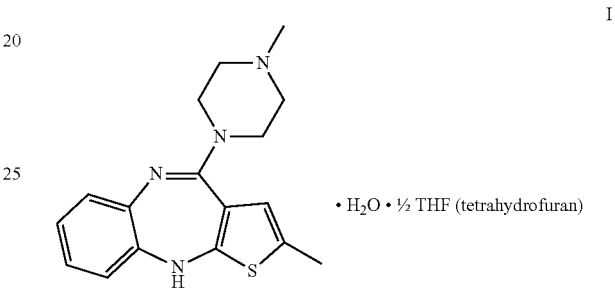

characterised in that it includes carrying out the following stages:

a) condensing the compound of formula (IIa) with piperazine of formula (IIIa) in the presence of at least one aprotic solvent, followed by purifying by crystallisation in anhydrous toluene:

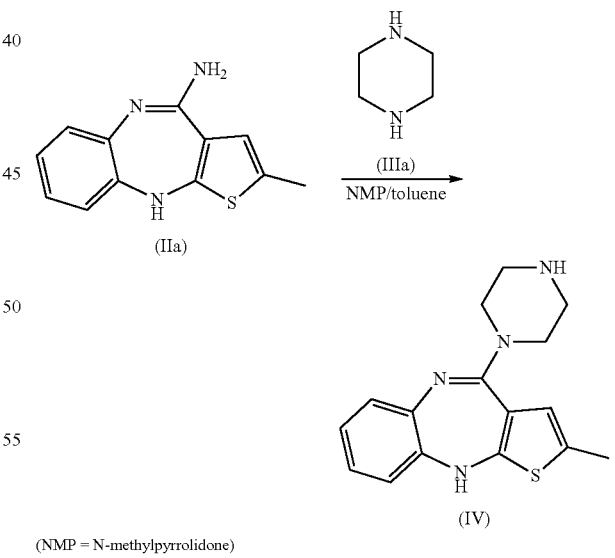

(NMP = N-methylpyrrolidone)

and b) methylating the N-desmethylolanzapine of formula (IV) with dimethyl sulphate in the presence of tetrahydrofuran and water as solvents, thereby directly obtaining the mixed solvate of olanzapine/water/tetrahydrofuran of formula I.

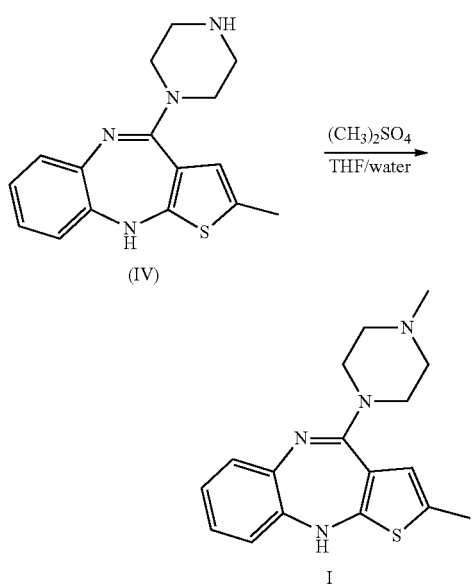

2. The method according to claim 1, characterised in that the reaction of stage a) is carried out with piperazine in the presence of N-methylpyrrolidone (NMP) and/or toluene or mixtures thereof.

3. The method according to claim 1, characterised in that said reaction of stage a) is carried out at a temperature between 50 and 150° C.

4. The method according to claim 3, characterised in that said reaction of stage a) is carried out at a temperature between 120 and 135° C.

5. The method according to claim 1, characterised in that said reaction of stage b) is carried out in the presence of at least one organic base selected from a hydroxide or a carbonate of an alkaline metal, in the presence of a mixture of THF (tetrahydrofuran) and water as solvent.

6. The method according to claim 1, characterised in that said reaction of stage b) is carried out at a temperature between 0 and 30° C., in an inert atmosphere.

7. The method according to claim 6, characterised in that said reaction of stage b) is carried out at a temperature between 5 and 15° C.

* * * * *